United States Patent
Rogerson et al.

(10) Patent No.: US 11,096,599 B1
(45) Date of Patent: Aug. 24, 2021

(54) SPHYGMOMANOMETER COVER/CUFF SYSTEM

(71) Applicants: Elaine Rogerson, Brooksville, FL (US); Luella Marston, Brooksville, FL (US)

(72) Inventors: Elaine Rogerson, Brooksville, FL (US); Luella Marston, Brooksville, FL (US)

(73) Assignee: ARMS WAY, LLC, Brooksville, FL (US)

( * ) Notice: Subject to any disclaimer, the term of this patent is extended or adjusted under 35 U.S.C. 154(b) by 0 days.

(21) Appl. No.: 16/288,962

(22) Filed: Feb. 28, 2019

Related U.S. Application Data

(63) Continuation-in-part of application No. 13/902,899, filed on May 27, 2013, now abandoned, which is a continuation-in-part of application No. 11/708,510, filed on Feb. 20, 2007.

(51) Int. Cl.
*A61B 5/022* (2006.01)
*A61B 5/021* (2006.01)
*A61B 46/10* (2016.01)
*A61B 50/00* (2016.01)

(52) U.S. Cl.
CPC ...... *A61B 5/02233* (2013.01); *A61B 5/02141* (2013.01); *A61B 46/10* (2016.02); *A61B 2050/005* (2016.02); *A61B 2562/247* (2013.01)

(58) Field of Classification Search
CPC .......... A61B 5/02233; A61B 2562/247; A41D 13/08
See application file for complete search history.

(56) References Cited

U.S. PATENT DOCUMENTS

| | | | | |
|---|---|---|---|---|
| 5,070,540 A | * | 12/1991 | Bettcher | A41D 19/0058 2/2.5 |
| 5,592,953 A | * | 1/1997 | Delao | A61F 15/004 128/882 |
| 5,628,062 A | * | 5/1997 | Tseng | A41D 13/08 2/16 |
| 5,644,793 A | * | 7/1997 | Lahaussois | A41D 13/08 2/16 |
| 5,669,390 A | * | 9/1997 | McCormick | A61B 5/02233 600/499 |
| 5,924,130 A | * | 7/1999 | Fragomeli | A41D 13/08 2/16 |
| 2010/0186752 A1 | * | 7/2010 | Rixson | A61B 5/02233 128/846 |
| 2016/0324429 A1 | * | 11/2016 | Maranville | A61B 5/02233 |
| 2018/0271187 A1 | * | 9/2018 | Mullings | A41D 13/08 |
| 2019/0110537 A1 | * | 4/2019 | Shigaki | A41D 19/02 |
| 2019/0230999 A1 | * | 8/2019 | Bozelko | A41B 13/00 |

OTHER PUBLICATIONS

Danlee Medical. Jun. 9, 2016. https://web.archive.org/web/20160609110509/https://www.danleemedical.com/Disposable-Blood-Pressure-Cuff-Protective-Liner-item-HCUBP-P165.aspx (Year: 2016).*

* cited by examiner

*Primary Examiner* — Meredith Weare

(57) ABSTRACT

Protecting a blood pressure cuff and its user is in a sanitary and convenient manner. A shield has upper and lower edges, longitudinal side edges, and interior and exterior surfaces. Stitching couples the side edges. The shield forms a funnel-shaped, generally conical configuration. The upper edge is imperforate, devoid of elastic, and has a first circumference. The shield is fabricated of a flexible material. A continuous elastic band is secured to the shield adjacent the lower edge. The elastic band is adapted to constrict the lower edge to a second circumference when in a relaxed, un-stretched orientation.

1 Claim, 4 Drawing Sheets

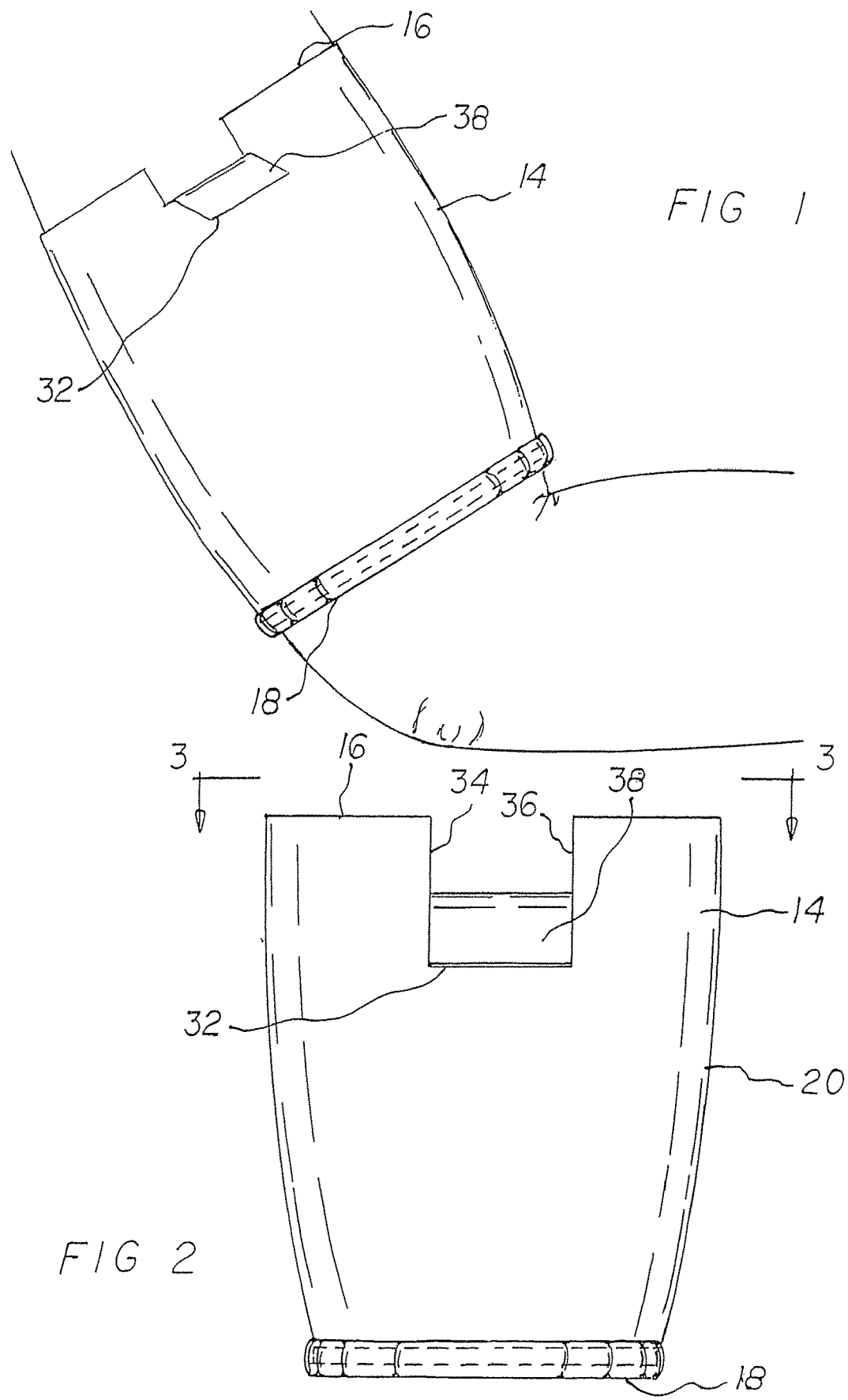

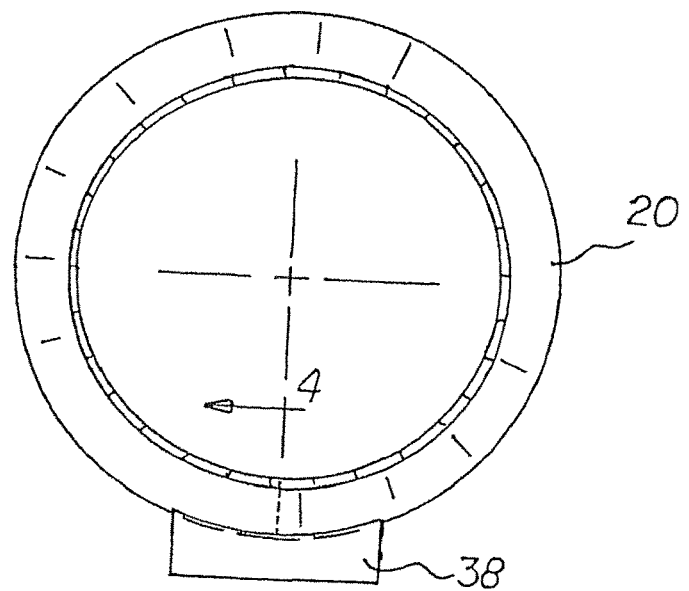
FIG 3
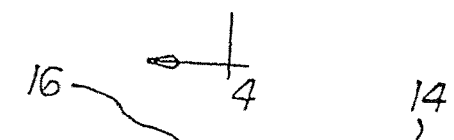
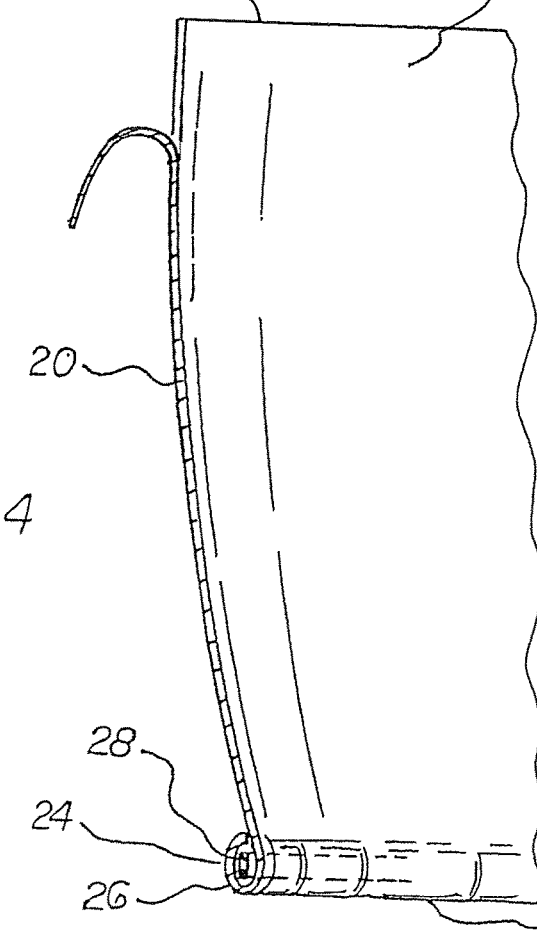
FIG 4

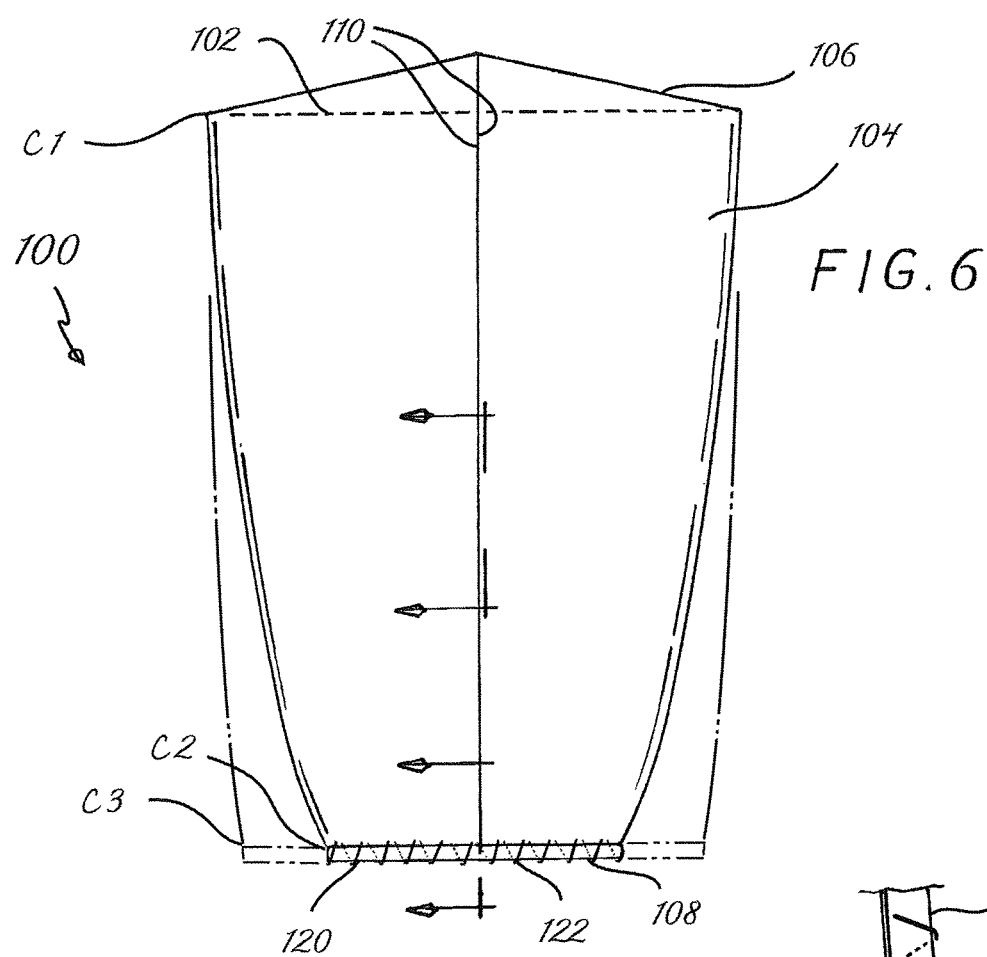
FIG. 6
FIG. 7
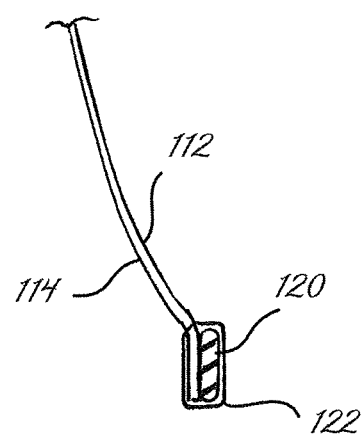
FIG. 8

SPHYGMOMANOMETER COVER/CUFF SYSTEM

RELATED APPLICATION

The present patent application is a continuation-in-part of U.S. patent application Ser. No. 13/902,899 filed May 27, 2013 which is a continuation-in-part of U.S. patent application Ser. No. 11/708,510, filed Feb. 20, 2007, the subject matter of which applications is incorporated herein by reference.

BACKGROUND OF THE INVENTION

Field of the Invention

The present invention relates to a sphygmomanometer cover/cuff system and more particularly pertains to protecting a blood pressure cuff and its user in a sanitary and convenient manner.

Description of the Prior Art

The use of sphygmomanometer covers is known in the prior art. More specifically, sphygmomanometer covers of known designs and configurations previously devised and utilized for the purpose of protecting sphygmomanometers and users are known to consist basically of familiar, expected, and obvious structural configurations, notwithstanding the myriad of designs encompassed by the crowded prior art which has been developed for the fulfillment of countless objectives and requirements.

By way of example, U.S. Pat. No. 3,473,525 issued Oct. 21, 1969 to Hanafin relates to a Disposable Sphygmomanometer. U.S. Pat. No. 4,967,758 issued May 6, 1990 to Masciarotte relates to a Disposable Coverliner for Blood Pressure Measuring Devices. U.S. Pat. No. 5,228,448 issued Jul. 20, 1993 to Byrd relates to a Protective Cover for Blood-Pressure Cuffs. U.S. Pat. No. 5,819,739 issued Oct. 13, 1998 to Levavi relates to a Method and Apparatus for Contravention of the Transfer of Pathogenic Organisms. U.S. Pat. No. 6,525,238 issued Feb. 25, 2003 to Corrales relates to a Single Use Disposable Skin and Cuff Protector.

While these devices fulfill their respective, particular objectives and requirements, the aforementioned patents do not describe a sphygmomanometer cover/cuff system that allows for the protection of a blood pressure cuff and its user in a sanitary and convenient manner.

In this respect, the sphygmomanometer cover/cuff system according to the present invention substantially departs from the conventional concepts and designs of the prior art, and in doing so provides an apparatus primarily developed for the purpose of protecting a blood pressure cuff and its user in a sanitary and convenient manner.

Therefore, it can be appreciated that there exists a continuing need for a new and improved sphygmomanometer cover/cuff system which can be used for protecting a blood pressure cuff and its user in a sanitary and convenient manner. In this regard, the present invention substantially fulfills this need.

SUMMARY OF THE INVENTION

In view of the foregoing disadvantages inherent in the known types of sphygmomanometer covers of known designs and configurations now present in the prior art, the present invention provides an improved sphygmomanometer cover/cuff system. As such, the general purpose of the present invention, which will be described subsequently in greater detail, is to provide a new and improved sphygmomanometer cover/cuff system and method which has all the advantages of the prior art and none of the disadvantages.

To attain this, the present invention essentially comprises a sphygmomanometer cover/cuff system for protecting a blood pressure cuff and its user in a sanitary and convenient manner. First provided is a shield having upper and lower edges and longitudinal side edges. The shield has interior and exterior surfaces. Stitching couples the side edges. The side walls forming a funnel-shaped, generally conical configuration. The shield being fabricated of a flexible, plastic material. Next provided is a continuous elastic band secured to the interior surface of the cover adjacent the lower edge. The elastic band is adapted to constrict the lower edge to a first circumference when in a relaxed, un-stretched orientation. The elastic band is adapted to extend the lower edge to a second circumference less than the first distance when in use in a stretched orientation. The upper edge is imperforate and devoid of elastic.

There has thus been outlined, rather broadly, the more important features of the invention in order that the detailed description thereof that follows may be better understood and in order that the present contribution to the art may be better appreciated. There are, of course, additional features of the invention that will be described hereinafter and which will form the subject matter of the claims attached.

In this respect, before explaining at least one embodiment of the invention in detail, it is to be understood that the invention is not limited in its application to the details of construction and to the arrangements of the components set forth in the following description or illustrated in the drawings. The invention is capable of other embodiments and of being practiced and carried out in various ways. Also, it is to be understood that the phraseology and terminology employed herein are for the purpose of descriptions and should not be regarded as limiting.

As such, those skilled in the art will appreciate that the conception, upon which this disclosure is based, may readily be utilized as a basis for the designing of other structures, methods and systems for carrying out the several purposes of the present invention. It is important, therefore, that the claims be regarded as including such equivalent constructions insofar as they do not depart from the spirit and scope of the present invention.

It is therefore an object of the present invention to provide a new and improved sphygmomanometer cover/cuff system which has all of the advantages of the prior art sphygmomanometer covers of known designs and configurations and none of the disadvantages.

It is another object of the present invention to provide a new and improved sphygmomanometer cover/cuff system which may be easily and efficiently manufactured and marketed.

It is further object of the present invention to provide a new and improved sphygmomanometer cover/cuff system which is of durable and reliable constructions.

An even further object of the present invention is to provide a new and improved sphygmomanometer cover/cuff system which is susceptible of a low cost of manufacture with regard to both materials and labor, and which accordingly is then susceptible of low prices of sale to the consuming public, thereby making such sphygmomanometer cover/cuff system economically available to the buying public.

Even still another object of the present invention is to provide a sphygmomanometer cover/cuff system for protecting a blood pressure cuff and its user in a sanitary and convenient manner.

Lastly, it is an object of the present invention to provide a new and improved sphygmomanometer cover/cuff system for positioning over an arm of a patient under a blood pressure cuff for protecting the patient and the blood pressure cuff, the positioning and the protecting being done in a safe, sanitary, convenient and economical manner.

These together with other objects of the invention, along with the various features of novelty which characterize the invention, are pointed out with particularity in the claims annexed to and forming a part of this disclosure. For a better understanding of the invention, its operating advantages and the specific objects attained by its uses, reference should be had to the accompanying drawings and descriptive matter in which there is illustrated preferred embodiments of the invention.

BRIEF DESCRIPTION OF THE DRAWINGS

The invention will be better understood and objects other than those set forth above will become apparent when consideration is given to the following detailed description thereof. Such description makes reference to the annexed drawings wherein:

FIG. 1 is a side elevational view of a sphygmomanometer cover/cuff system for protecting a blood pressure cuff and its user.

FIG. 2 is a front elevational view of the sphygmomanometer cove/cuff system shown in FIG. 1.

FIG. 3 is a plan view of the sphygmomanometer cover/cuff system taken along line 3-3 of FIG. 2.

FIG. 4 is a cross-sectional view taken along line 4-4 of FIG. 3.

FIG. 6 is a front elevational view of a sphygmomanometer cover/cuff system constructed in accordance with the final embodiment of the invention.

FIG. 7 is a cross sectional view of the longitudinal seam of the shield taken long line 7-7 of FIG. 6.

FIG. 8 is a cross sectional view of the circumferential seam of the shield taken long line 8-8 of FIG. 6.

The same reference numerals refer to the same parts throughout the various Figures.

DESCRIPTION OF THE PREFERRED EMBODIMENT

Figure 5:
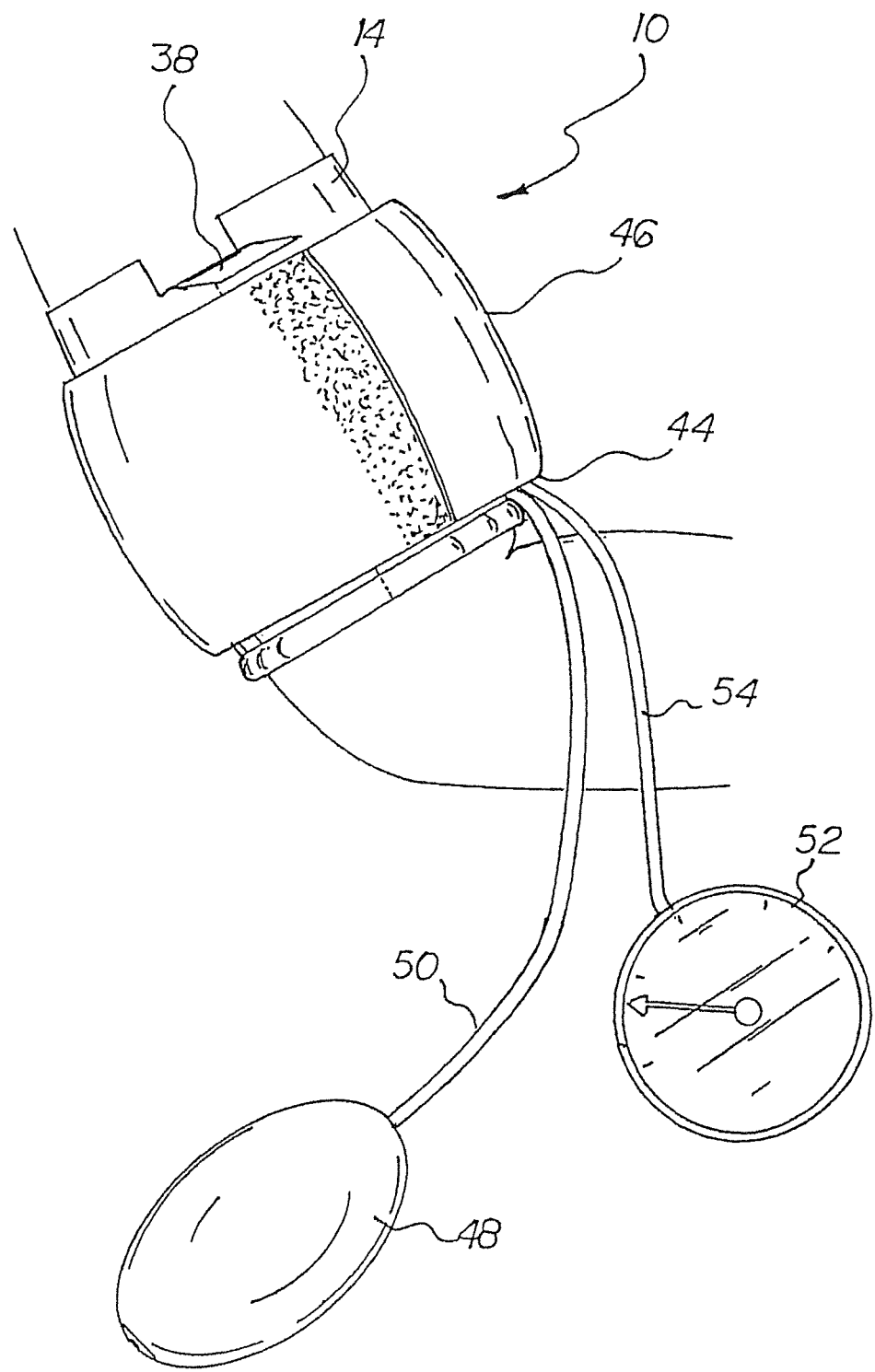
FIG. 5 is a side elevational view of a sphygmomanometer cover/cuff system similar to FIG. 1 but with the sphygmomanometer in operative position.

With reference now to the drawings, and in particular to FIG. 1 thereof, the preferred embodiment of the new and improved sphygmomanometer cover/cuff system embodying the principles and concepts of the present invention and generally designated by the reference numeral 10 will be described.

The present invention, the sphygmomanometer cover/cuff system 10 is comprised of a plurality of components. Such components in their broadest context include a shield, a constriction assembly, and a handling assembly. Such components are individually configured and correlated with respect to each other so as to attain the desired objective.

The sphygmomanometer cover/cuff system 10 protects a blood pressure cuff and its user in a sanitary and convenient manner. First provided is a shield 14 having an upper peripheral edge 16 and a lower peripheral edge 18. A generally cylindrical cone-shaped side wall 20 is provided between the edges. The shield is fabricated of a flexible material, preferably paper. The shield has a central axis with an axial length of between about 6 inches and inches, preferably about 9 inches. The shield has a circumference of between about 6 inches and 20 inches, preferably about 16 inches.

A constriction assembly 24 is next provided. The constriction assembly is formed as a circumferential loop 26 around the lower peripheral edge of the shield with a continuous elastic band 28 within the loop. The continuous elastic band has a relaxed circumference of between about 4 inches and 18 inches, preferably about 6 inches.

A handling assembly 32 is next provided. The handling away assembly is formed at the upper peripheral edge of the shield and includes two short axial slits 34, 36 extending axially downwardly to define a pull tab 38 between the slits. The slits are laterally spaced by between about 1 inch and 4 inches, preferably about 1.5 inches. The slits have an axial length of between about 1 inches and 2 inches, preferably about 1.5 inches. The upper peripheral edge is discontinuous due to the slits. The shield is positionable on an arm of a user at the elbow. When the shield is in position, the lower peripheral edge is located immediately above the elbow, the upper peripheral edge is adjacent to the shoulder, and the handling assembly is on a distal portion of the arm. In this manner easy access is for pulling up the shield for easy slide on/off application by a care giver and for disposal.

Next provided is a sphygmomanometer 44. The sphygmomanometer includes a circumferential cuff 46. Also included is a squeeze ball 48 with a first line 50 for inflating the cuff and a meter 52 with a second line 54 for displaying a measured blood pressure. The cuff is positionable over an arm of a user with the shield between the arm and the cuff to protect the user from contact with the cuff and to protect the cuff from contact with user. The cuff has an axial length less than that of the shield to expose the lower peripheral edge and the upper peripheral edge including the tab. In this manner handling of the shield for sliding it on and sliding it off of a user and disposal is facilitated.

Illustrated in FIGS. 6-8 is a final alternate embodiment of the invention. Such invention is a sphygmomanometer cover/cuff system 100 for positioning over an arm of a patient under a blood pressure cuff for protecting the patient and the blood pressure cuff. The positioning and the protecting is done in a safe, sanitary, convenient and economical manner.

First provided is a shield 104 having an upper peripheral edge 102, 106 and a lower peripheral edge 108 and longitudinal side edges 110. The shield has a front and a back. The upper and lower peripheral edges at the back 102 are parallel and spaced by a axial length first distance of 9.5 inches plus or minus 20 percent. The upper edge at the front 106 106b is formed as an isosceles triangle with a height of 0.375 inches plus or minus 20 percent. The shield has an interior surface 112 and an exterior surface 114. The exterior surface at the longitudinal side edges is in mutual contact with primary overcast stitching 116 contacting and encompassing the longitudinal side edges. The longitudinal side edges dividing the isosceles triangle into two similarly smaller triangles. The shield forms a funnel-shaped, generally conical configuration with a central axis between the upper and lower peripheral edges. The shield has a central axis. The shield has a circumference at the upper peripheral edge of 20 inches plus or minus 20 percent. The shield is fabricated of a flexible, plastic material.

Next provided is a continuous elastic band 120 secured to the interior surface of the shield adjacent the lower peripheral edge. Secondary overcast stitching to 122 contacts and encompasses the lower peripheral edge and the continuous elastic band. The elastic band is adapted to constrict the lower peripheral edge to a circumference of 10 inches plus or minus 20 percent when in a relaxed, un-stretched orientation. The elastic band is adapted to extend the lower peripheral edge to a circumference of 16 inches plus or minus 20 percent when in use in a fully stretched orientation. The upper peripheral edge is imperforate and devoid of elastic whereby the upper peripheral edge of the shield is adapted to be grasped by one hand of a care giver with the patient extending an arm into and through the shield, upper peripheral edge first, due to the funnel-shaped, generally conical configuration of the shield.

The upper peripheral edge has a first circumference C-1. The elastic band is adapted to constrict the lower peripheral edge to a second circumference C-2 when in a relaxed, un-stretched orientation. The lower peripheral edge is adapted to attain a third circumference C-3 when stretched to the maximum. The third circumference is less than the first circumference and greater than the second circumference Lastly, a sphygmomanometer 44 is provided. It includes a circumferential blood pressure cuff 46 and a squeeze ball 48 with a first line 50 for inflating the cuff. It also includes a meter 52 with a second line 54. The meter is for displaying a measured blood pressure. The cuff is positionable over and around an arm of the patient with the shield between the arm and the cuff to protect the patient from contact with the cuff and to protect the cuff from contact with the patient. The cuff has an axial length less than the axial length of the shield to expose the lower peripheral edge and the upper peripheral edge for facilitating the handling of the shield at the isosceles triangle during sliding on and sliding off of the patient.

As to the manner of usage and operation of the present invention, the same should be apparent from the above description. Accordingly, no further discussion relating to the manner of usage and operation will be provided.

With respect to the above description then, it is to be realized that the optimum dimensional relationships for the parts of the invention, to include variations in size, materials, shape, form, function and manner of operation, assembly and use, are deemed readily apparent and obvious to one skilled in the art, and all equivalent relationships to those illustrated in the drawings and described in the specification are intended to be encompassed by the present invention.

Therefore, the foregoing is considered as illustrative only of the principles of the invention. Further, since numerous modifications and changes will readily occur to those skilled in the art, it is not desired to limit the invention to the exact construction and operation shown and described, and accordingly, all suitable modifications and equivalents may be resorted to, falling within the scope of the invention.

What is claimed as being new and desired to be protected by Letters Patent of the United States is as follows:

1. A sphygmomanometer shield system for positioning over an arm of a patient, the system consisting of:
    a funnel-shaped, generally conical shield having a front, a back, an upper peripheral edge, a lower peripheral edge, longitudinal side edges, an interior surface, an exterior surface, and a central axis between the upper and lower peripheral edges, wherein:
        the upper and lower peripheral edges at the back are parallel and spaced by an axial length of 9.5 inches plus or minus 20 percent,
        the entire front upper peripheral edge forms an isosceles triangle with a height of 0.375 inches plus or minus 20 percent,
        the isosceles triangle of the upper peripheral edge of the shield functions as a gripping component and is adapted to be grasped by one hand of a care giver to provide tension across the upper peripheral edge of the shield with the patient extending his/her arm into and through the shield, upper peripheral edge first,
        the longitudinal side edges are in mutual contact with first stitching and divide the isosceles triangle into two similarly configured smaller triangles,
        the shield is formed of a single sheet of flexible, plastic material sewn together at the longitudinal ends, and
        the upper peripheral edge is devoid of elastic and has a first circumference C-1 of 20 inches plus or minus 20 percent;
    a continuous elastic band secured to the interior surface of the shield adjacent the lower peripheral edge, wherein second stitching contacts and encompasses the lower peripheral edge and the continuous elastic band, wherein the elastic band is adapted to constrict the lower peripheral edge to a circumference C-2 of 10 inches plus or minus 20 percent when in a relaxed, unstretched orientation, and allow extension of the lower peripheral edge to a third circumference C-3 of 16 inches plus or minus 20 percent when in use in a fully stretched orientation, and wherein the third circumference C-3 is less than the first circumference C-1 and greater than the second circumference C-2; and
    a sphygmomanometer including a circumferential cuff, a squeeze ball for inflating the cuff, and a meter for displaying a measured blood pressure, wherein the cuff is positionable over and around an arm of the patient with the shield between the arm and the cuff to protect the patient from contact with the cuff and to protect the cuff from contact with the patient, and wherein the cuff has an axial length less than the axial length of the shield to expose the lower peripheral edge and the upper peripheral edge to facilitate handling of the shield at the isosceles triangle when sliding the shield on and off of the arm of the patient.

* * * * *